(12) United States Patent
Guth et al.

(10) Patent No.: US 7,404,311 B2
(45) Date of Patent: Jul. 29, 2008

(54) BREATH TEST SIMULATOR

(75) Inventors: Richard U Guth, Harrisburg, PA (US); David A. Fisher, Harrisburg, PA (US)

(73) Assignee: Guth Laboratories, Inc., Harrisburg, PA (US)

( * ) Notice: Subject to any disclaimer, the term of this patent is extended or adjusted under 35 U.S.C. 154(b) by 149 days.

(21) Appl. No.: 11/530,489

(22) Filed: Sep. 11, 2006

(65) Prior Publication Data
US 2008/0060408 A1    Mar. 13, 2008

(51) Int. Cl.
G01N 33/497 (2006.01)
G01N 1/22 (2006.01)
G12B 13/00 (2006.01)
G01C 25/00 (2006.01)

(52) U.S. Cl. ............ 73/1.03; 73/23.3; 73/23.34; 73/863.11; 73/863.81; 422/83; 422/84; 436/9

(58) Field of Classification Search ........... 73/1.03, 73/1.04, 1.06, 23.3, 23.34, 863.11, 863.81; 422/83–85; 436/9
See application file for complete search history.

(56) References Cited

U.S. PATENT DOCUMENTS

| 3,520,194 | A |   | 7/1970  | Adams ..................... 73/1 |
| 3,854,319 | A |   | 12/1974 | Burroughs et al. ......... 73/1 |
| 3,904,849 | A |   | 9/1975  | Luccro et al. ........... 219/299 |
| 3,982,095 | A |   | 9/1976  | Robinson ............... 219/273 |
| 4,003,240 | A |   | 1/1977  | Durbin .................... 73/1 |
| 4,009,713 | A |   | 3/1977  | Simmons et al. ........ 128/193 |
| 4,028,444 | A |   | 6/1977  | Brown et al. ........... 261/122 |
| 4,028,445 | A |   | 6/1977  | Hickmann et al. ...... 261/142 |
| 4,036,915 | A |   | 7/1977  | Lucero et al. .......... 261/104 |
| 4,036,919 | A |   | 7/1977  | Komendowski et al. ... 261/122 |
| 4,101,611 | A |   | 7/1978  | Williams ............... 261/142 |
| 4,407,152 | A |   | 10/1983 | Guth ....................... 73/1 |
| 4,412,526 | A | * | 11/1983 | DeGrose ................ 122/14.1 |
| 4,474,048 | A |   | 10/1984 | Schmidt .................... 73/1 |
| 4,567,748 | A |   | 2/1986  | Klass et al. ................ 73/1 |
| 4,923,306 | A | * | 5/1990  | Fauske .................... 374/34 |
| 5,191,211 | A | * | 3/1993  | Gorman, Jr. ............ 250/282 |
| 5,266,496 | A | * | 11/1993 | Dacruz ................... 436/157 |
| 5,337,619 | A | * | 8/1994  | Hodgins et al. ....... 73/863.11 |
| 5,363,707 | A | * | 11/1994 | Augenblick et al. .... 73/864.84 |
| 5,528,923 | A | * | 6/1996  | Ledez et al. ............ 73/19.12 |
| 5,578,495 | A | * | 11/1996 | Wilks .................... 436/178 |
| 5,731,508 | A |   | 3/1998  | Slemeyer ............... 73/1.03 |
| 5,773,707 | A | * | 6/1998  | Scheppers et al. ...... 73/1.03 |
| 6,096,558 | A | * | 8/2000  | Stock .................... 436/132 |
| 6,436,710 | B1| * | 8/2002  | Sivavec et al. ........... 436/39 |
| 6,526,802 | B1|   | 3/2003  | Fisher et al. ........... 73/1.03 |
| 6,706,245 | B2| * | 3/2004  | Neal et al. .............. 422/100 |
| 6,815,216 | B2| * | 11/2004 | Sandra et al. ........... 436/178 |
| 7,082,849 | B2| * | 8/2006  | Chida et al. .......... 73/864.52 |
| 2005/0232074 | A1| * | 10/2005 | Higashihara et al. ...... 366/273 |
| 2006/0213252 | A1| * | 9/2006  | Jen ..................... 73/23.2 |

* cited by examiner

*Primary Examiner*—David A. Rogers
(74) *Attorney, Agent, or Firm*—Hooker & Habib, P.C.

(57) ABSTRACT

A breath simulator for supplying a breath test analyzer with a sample effluent of ethyl alcohol that controls headspace and adjacent effluent passageway temperature.

18 Claims, 3 Drawing Sheets

BREATH TEST SIMULATOR

FIELD OF THE INVENTION

The invention relates to breath simulators that supply sample effluent containing a precisely controlled concentration of ethyl alcohol to a breath test analyzer for calibrating the analyzer.

DESCRIPTION OF THE PRIOR ART

The alcohol content in the breath of an individual is an indicator of alcohol content in the blood of the individual. Breath test analyzers are commonly used to determine the alcohol content in the blood of an individual, typically the driver of a motor vehicle, by determining the alcohol content in the breath of the individual.

Breath test analyzers must be calibrated to maintain accuracy. A known means of calibrating an analyzer is to use a breath test simulator that flows air through a solution of water and ethyl alcohol of known concentration to generate a breath test effluent sample having a known alcohol concentration. The effluent sample is flowed to an analyzer to calibrate the analyzer. Breath test simulators must provide breath test effluent samples having precisely controlled ethyl alcohol concentrations in order to calibrate breath test analyzers accurately.

Breath test simulators of the type disclosed in Fisher et al. U.S. Pat. No. 6,526,802 are known. These simulators include a sealed jar containing a water-alcohol solution of known concentration and an effluent headspace over the solution. An immersion heater heats the solution to a desired temperature while a stirrer circulates the solution to assure even heating. An immersion sensor in the solution monitors the temperature of the solution. When the solution is at the desired temperature, outside air is bubbled through the solution. Air bubbled through the solution absorbs a known amount of ethyl alcohol from the solution and is collected in the headspace above the solution. This effluent is then flowed from the headspace to a breath test analyzer to calibrate the analyzer.

Breath test samples flowed to analyzers for calibrating the analyzers must have a known concentration of ethyl alcohol. This concentration may vary slightly within an acceptable range. More accurate control of the concentration of ethyl alcohol in the breath test sample is desirable and permits calibrating the analyzer more accurately so that the analyzer conducts breath tests with improved accuracy.

In known breath test simulators, headspace temperature is dependent on the temperature of the water-alcohol solution below it. As air is bubbled through the solution to form a breath test effluent sample in the headspace, headspace temperature decreases due to evaporation and the cooler temperature of air. The heater immersed in the solution does not directly heat the sample in the headspace to compensate for this temperature drop. The temperature of the effluent produced by the simulator and the alcohol concentration of the effluent would be more accurately controlled by controlling the temperature of the air and vapor in the headspace.

Breath test effluent passes through an outlet passage leading to the analyzer. Heat loss in the passage can effect the alcohol concentration in the effluent and cause condensation. Calibration accuracy of simulators would be improved by heating the outlet passage to maintain temperature of the effluent and prevent condensation.

Therefore, there is a need for a breath test simulator that precisely controls headspace temperature to allow reliable generation of breath test effluent having a known concentration of ethyl alcohol.

SUMMARY OF THE INVENTION

The invention is a breath test simulator with a headspace heater. The simulator has a sealed jar containing an ethyl alcohol-water solution of known concentration and a headspace over the solution. An immersion heater maintains the solution at a desired temperature. The headspace heater precisely controls the temperature of breath test effluent located in the headspace. The headspace heater also heats an effluent outlet passage leading to the analyzer.

The simulator includes a black anodized aluminum jar lid heated by a resistor. A temperature sensor on the lid actuates a switch to activate the resistor when the temperature of the lid falls below a desired temperature and to deactivate the resister when a desired temperature is reached. The resistor heats the lid by conduction so that heat radiates evenly down from the lid into the headspace and heats the effluent in the headspace. Heat also radiates up from the lid and heats the effluent outlet passage.

The invention allows very precise temperature control of effluent samples flowed to breath test analyzers to improve the accuracy of analyzer calibration.

Other objects and features of the invention will become apparent as the description proceeds, especially when taken in conjunction with the accompanying drawings illustrating the invention.

DESCRIPTION OF THE PREFERRED EMBODIMENTS

Figure 1:
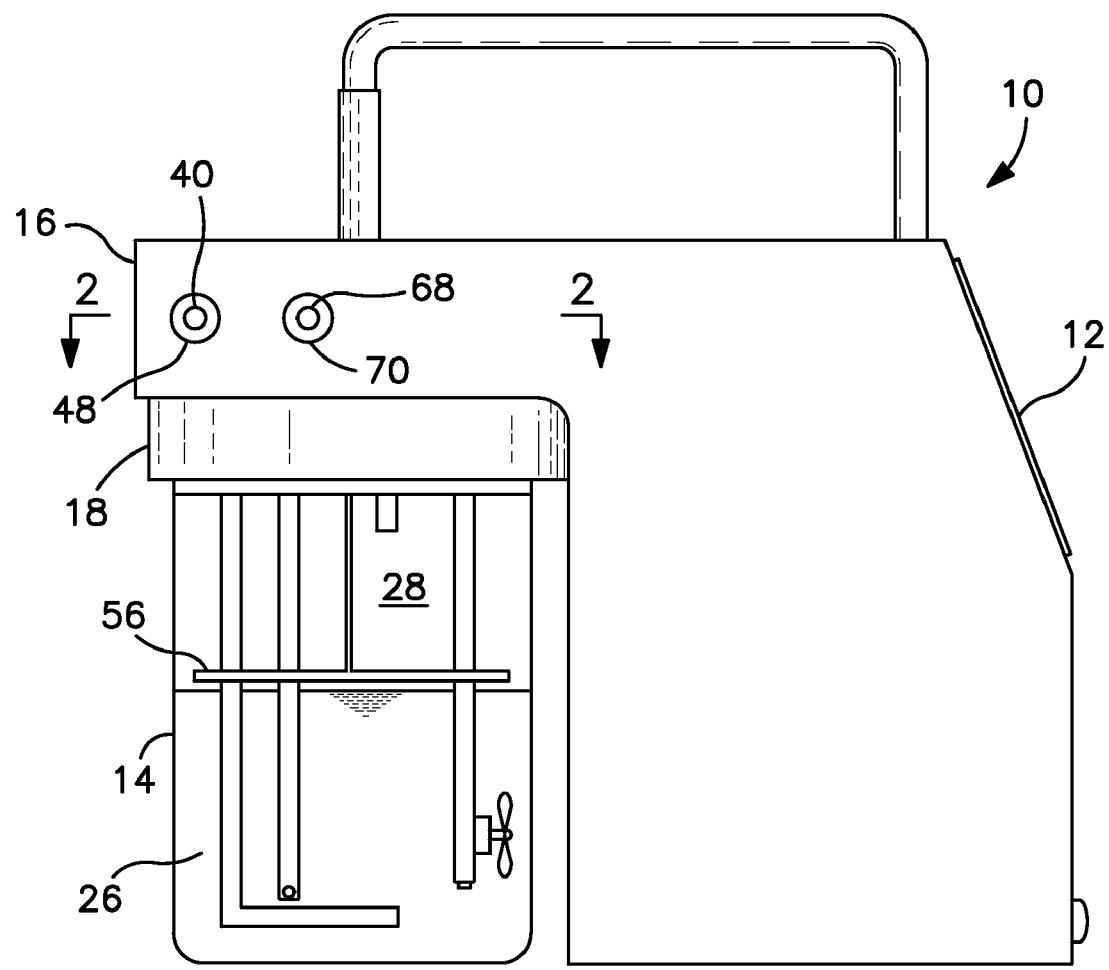
FIG. 1 is a side view of the breath test simulator.
Figure 2:
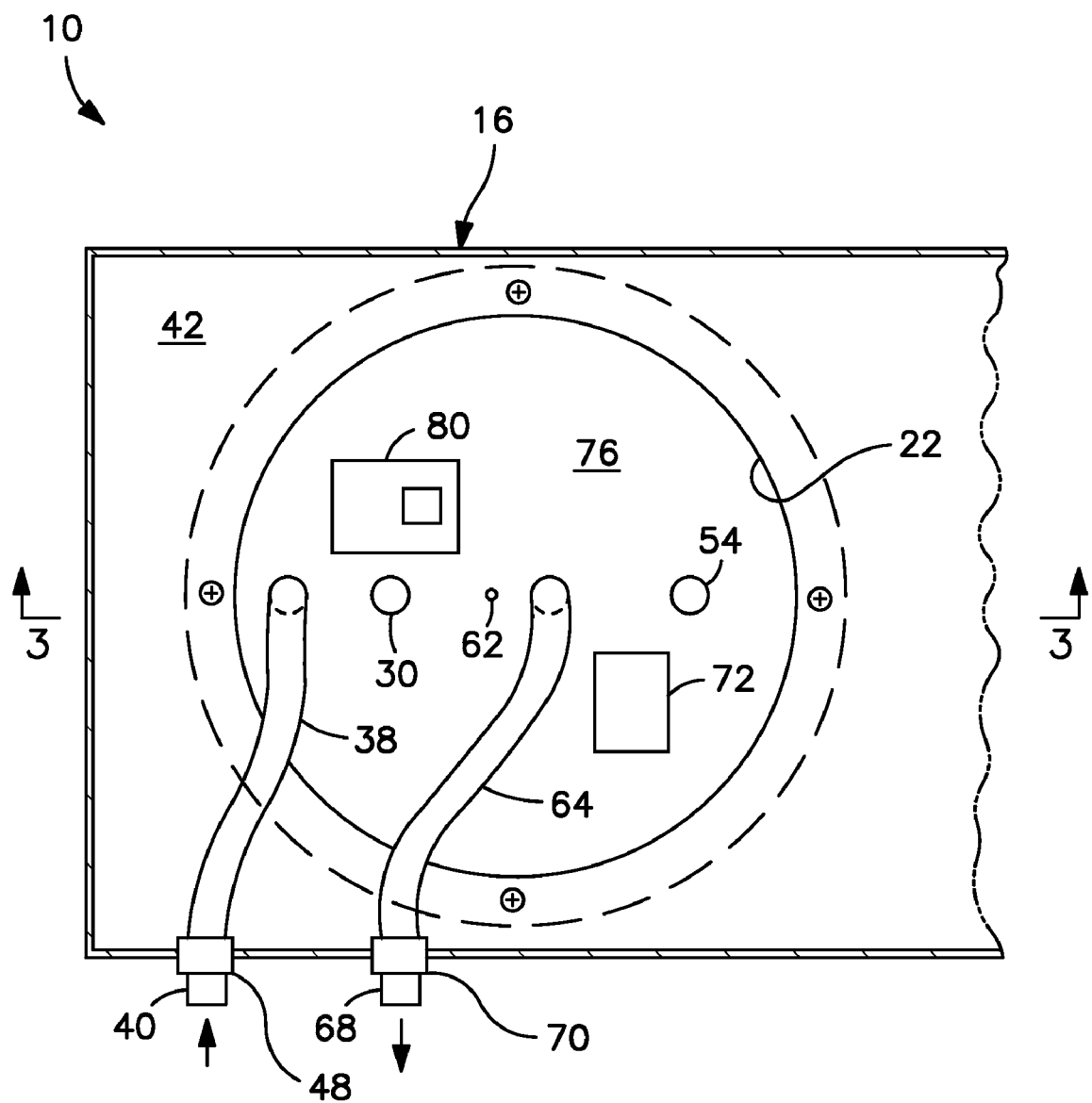
FIG. 2 is a sectional view taken along line 2-2 of FIG. 1.
Figure 3:
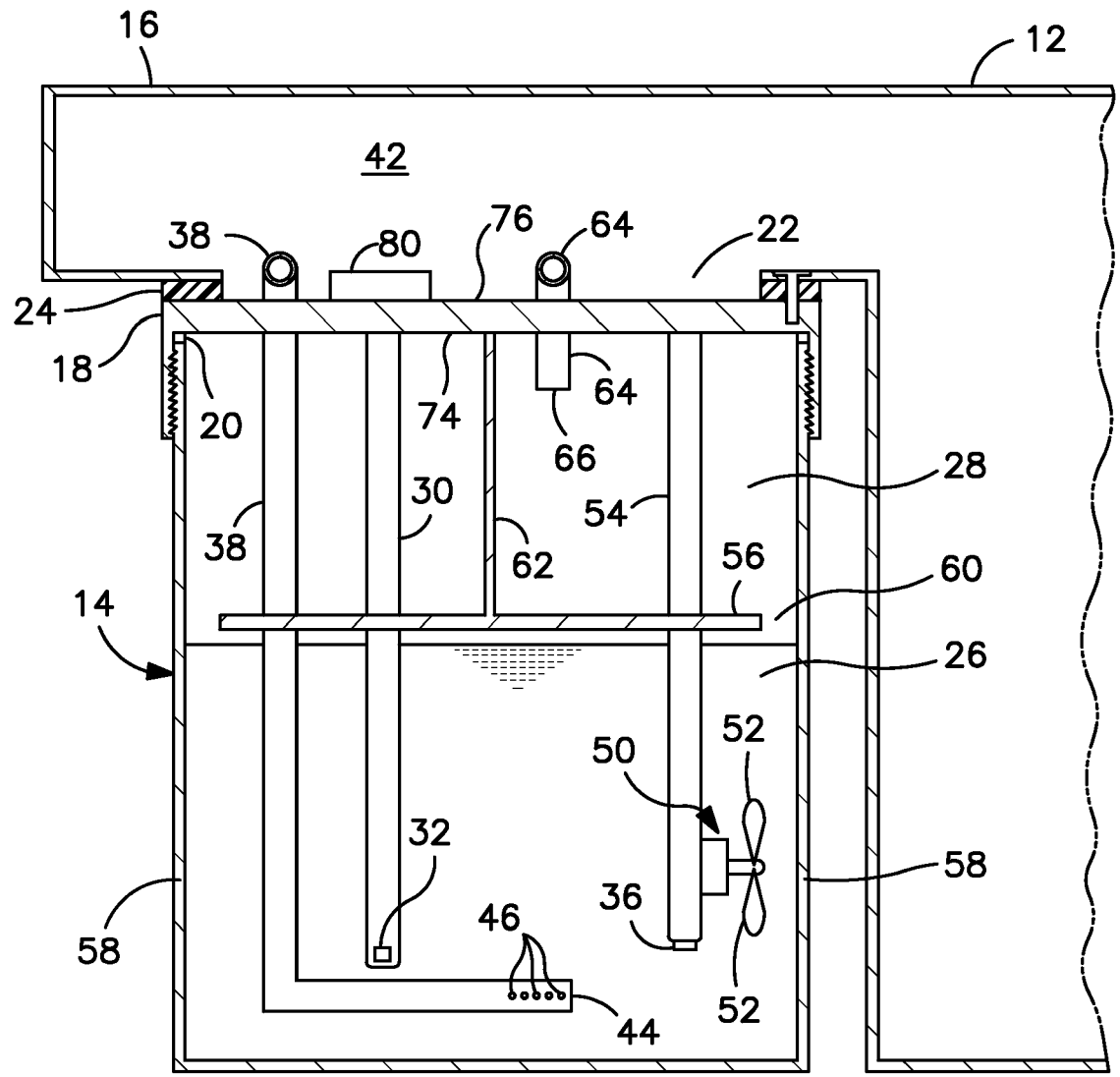
FIG. 3 is a sectional view taken along line 3-3 of FIG. 2.

The first embodiment breath test simulator 10 disclosed herein relates to the breath test simulator of Fisher et al. U.S. Pat. No. 6,526,802, the disclosure of which is incorporated herein by reference in its entirety.

Portable breath test simulator 10 includes a case or body 12 and a sealed container or jar 14. Jar 14 is mounted on the underside of support arm 16 extending outwardly from one side of body 12.

Container 14 may be a plastic jar that is screwed into lid 18 mounted on the underside of support arm 16. A circumferential gasket 20 is mounted on the lower surface of the lid to engage the top of the jar and prevent leakage into or out of the interior of the chamber 14. Lid 18 is mounted under opening 22 in the lower wall of arm 16. A circumferential thermal gasket 24 is provided between lower wall of the arm and the lid to prevent the lid from heating the arm.

Jar 14 is partially filled with an ethyl alcohol-water solution 26 of known concentration. An effluent headspace or chamber 28 in the jar is located above the top of solution 26 and below lid 18.

Arm 16 and lid 18 support a number of components that extend downwardly into jar 14. Immersion heater tube 30 extends through lid 18 and down into the solution in jar 14. Heater tube 30 includes an immersion solution heater 32 at the lower end thereof for heating the solution in the jar. The solution heater may be a resistance heater or other type of heater, including a small halogen light bulb.

Air inlet or blow tube 38 extends from inlet port 40 located to one side of arm 16, though the arm sidewall, through inner arm space 42 and to and down through lid 18 into jar 14. Closed lower end 44 of the blow tube is located in the solution adjacent to the bottom of jar 14. A number of small diameter air dispersion holes or air outlets 46 extend through the immersed end of tube 38 adjacent lower end 44 to disperse air blown through tube 38 and out holes into the alcohol-water solution in the jar. Port 40 is mounted on arm 16 by insulating gasket 48.

Stirrer mechanism 50 is mounted on lid 18 and includes post 54 which extends down into jar 14. The stirrer mechanism includes magnetically actuated stirrer vanes 52 on the immersed end of the post having magnets mounted in the outer end of each vane for actualization by a magnetic stirrer drive mounted on body 12 adjacent the jar. Solution temperature sensor 36 is mounted on the lower end of post 54. Alternatively, post 54 may be eliminated and the stirrer mechanism and sensor 36 may be mounted on another component that extends downward into jar 14.

A horizontal baffle plate 56 is located in the jar above the top surface of solution 26 in the bottom of the jar to prevent air bubbled up through the solution from drawing liquid droplets of solution into headspace 28. Heater tube 30, air inlet tube 38 and post 54 extend through openings formed in the baffle plate. The baffle plate is spaced inwardly from the container sidewalls 58 to define a narrow gap 60 between the baffle plate and the sides of the chamber. The baffle plate is supported by post 62 mounted on lid 18.

Air outlet tube 64 extends from effluent inlet end 66 located in the top of effluent headspace 28, through lid 18, through arm space 42, through a sidewall of arm 16 to effluent outlet port 68, mounted in outlet insulating gasket 70 in the sidewall adjacent inlet port 40. The portion of tube 64 extending from lid 18 to port 68 is directly above lid 18.

Electric resistance heater 72 is mounted to the top of lid 18. The heater is in direct contact with the lid to efficiently transmit heat to the lid. Lid lower surface 74 faces headspace 28 and forms a headspace wall. Upper lid surface 76 faces space 42. Lid 18 is formed from heat conductive material, which may be aluminum. Surfaces 74 and 76 are dark and preferably anodized black. Black surface 76 enhances flow of heat from heater 72 into lid 18. Black surfaces 74 and 76 enhance even radiation of heat from lid 18 into headspace 28 and into the immersion space 42.

A set point switch control unit 80 includes a temperature sensor on surface 76 and control circuitry for flowing electricity through the resistor 72 when the temperature of the lid falls below an on set point temperature and stopping the flow when the temperature of the lid rises to an off set point temperature. The on set point temperature may be 35.8° C. and the off set point temperature may be 36.0° C. While the temperature of the lid is maintained between 35.8° C. and 36.0° C., the heated lid maintains the temperature of the breath test sample vapor in the headspace at 34.0° C. Control unit 80 may be part No. DS1620 manufactured by Dallas Semiconductors of Dallas, Tex. The unit 80 is mounted on the upper surface 76 of the lid in direct heat flow contact with the lid.

The aluminum lid may have a thickness of about 0.1 inches and has an appreciable heat sink mass for receiving heat from heater 72 and evenly radiating heat through black surface 74 into the headspace 28 and through black surface 76 into arm space 42. The relatively large mass of thick lid 18 assures that heat is radiated evenly down into the headspace 28 to heat effluent in the headspace. Heat is also radiated upwardly into arm space 42 to heat the portion of air outlet tube 64 in the arm space and heat effluent flowing through tube 64 to heat the effluent and prevent condensation in the tube.

Operation of breath test simulator 10 will now be described.

Sensor 36 for immersion heater 32 activates the heater to maintain the alcohol-water solution 26 at a temperature 34° C. Stirrer mechanism 50 circulates the solution in the jar to ensure even temperature.

Simultaneously, the headspace temperature sensor in unit 80 monitors the temperature of lid 18. If the temperature of the lid falls to 35.8° C., the unit activates heater 72 to heat the lid to 36° C. in order to heat the temperature of effluent in headspace 28 to 34° C. Heat loss prevents the lid from heating the effluent above 34° C. The thick aluminum lid 18 readily conducts heat so that heater 72 heats the entire lid and heat is evenly radiated down into the headspace from surface 74. The black anodized surface 74 facilitates heat flow into the headspace from the lid.

Heat is also radiated from black anodized surface 76 into arm space 42 to heat tube 64. The heated tube 64 heats effluent flowing through the tube and prevents condensation.

Simulator 10 may be used to calibrate a breath test analyzer when the solution in jar 14 reaches a temperature of 34° C. and the lid is heated to a temperature of 36° C. described.

Breath test analyzers are calibrated by attaching a blow tube to inlet port 40 on arm 16. The blow tube preferably includes a breath test mouthpiece or trap that captures solids contained in the breath flowed through the tube to prevent solids from entering air inlet tube 38 and clogging dispersion holes 46. The mouthpiece may be of the type disclosed in Guth, U.S. Pat. No. 4,292,978. A discharge tube is attached to outlet port 68. The other end of the discharge tube is connected to the breath test inlet of the analyzer being tested.

A breath test effluent sample is produced for calibrating an analyzer by an operator blowing air into the mouthpiece, though the blow tube, air inlet tube 38 and out holes 46. Bubbles formed at dispersion holes 46 rise up through the alcohol-water solution and absorb alcohol vapor and water vapor in equilibrium with the alcohol-water solution in jar 14. The bubbles form an effluent that flows up from the solution, past baffle plate 56 and into headspace 28. The baffle plate prevents solution droplets from flowing into the headspace. The effluent closely simulates human breath and contains a precisely known concentration of alcohol vapor.

The blowing of outside air into chamber 14 decreases the temperature in headspace 28, and outlet tube 64. As headspace 28 cools, lid 18 cools. In reaction to the cooling of the lid, control unit 80 activates heater 72 to heat the lid and surfaces 74 and 76. Heat in the lid radiates down from black anodized surface 74 to evenly heat the headspace to the desired temperature of 34° C.

The control circuitry will cycle the solution heater and the headspace effluent heater on and off through operation of the simulator to maintain effluent samples at the proper temperature as desired.

Blowing of outside air into jar 14 increases the pressure in the jar and flows the effluent in headspace 28 through outlet tube 64 and to an analyzer being tested. The alcohol in the effluent is measured by the analyzer to generate an analyzer breath alcohol readout. If the readout is high, the analyzer must be adjusted to lower the reading to the known alcohol concentration. If the readout is low, the analyzer must be adjusted to increase the readout. No adjustment is required if the readout is accurate.

The simulator may be programmed to produce samples of alcohol effluent having a desired concentration at a temperature other than 34° C. The simulator can be programmed to activate the solution heater and headspace heater at variable temperature set points.

In an alternative embodiment, the headspace 28 may be heated by a heater or heaters mounted on the lid and extending down into the headspace. A temperature sensor may be mounted on the bottom of the lid in order to directly sense headspace temperature and activate and deactivate the heater or heaters as required to maintain desired headspace temperature. In both embodiments heat is radiated into the headspace by a heated wall defining the headspace.

While we have illustrated and described preferred embodiments of our invention, it is understood that this is capable of modification, and we therefore do not wish to be limited to the precise details set forth, but desire to avail ourselves of such changes and alterations as fall within the purview of the following claims.

What we claim as our invention:

1. A breath test simulator for producing breath test effluent having a controlled concentration of ethyl alcohol, the simulator comprising: a body comprising a jar and a lid defining a chamber; the lid comprising a heat conductive body; a liquid solution in the chamber, the solution comprising water and ethyl alcohol and having a known concentration of ethyl alcohol; a headspace in the chamber located above the solution in the chamber; a headspace heating member having a heating surface facing the headspace and located above the solution, the headspace heating member comprising a resistance heater on the heat conductive body; a temperature sensor on the heat conductive body; and a set point switch responsive to the sensor to activate and deactivate the resistance heater; an inlet tube having an air inlet end located outside the chamber, the inlet tube extending from the inlet end into the chamber to an air outlet end in the solution; an effluent outlet tube having an effluent inlet end located in the headspace, the effluent outlet tube extending from the inlet end out of the chamber to an effluent outlet end located outside the chamber; wherein the headspace heating member heats alcohol-water effluent in the headspace.

2. The breath test simulator of claim 1 including an immersion heater located in the liquid solution.

3. The breath test simulator of claim 1 wherein the outlet tube is proximate the headspace heating member, wherein the heating member heats the outlet tube to heat effluent in the tube.

4. The breath test simulator of claim 1 wherein the conductive body is aluminum and includes a black heating surface facing the headspace.

5. The breath test simulator of claim 1 wherein the headspace heating member maintains the temperature of the effluent in the headspace substantially the same as the temperature of the solution in the jar.

6. The breath test simulator of claim 1 wherein the conductive member includes a heating surface facing the headspace.

7. A breath test simulator for producing breath test effluent having a controlled concentration of ethyl alcohol, the simulator comprising: a body comprising a jar and a lid defining a chamber; the lid comprising a heat conductive body; a liquid solution in the chamber, the solution comprising water and ethyl alcohol and having a known concentration of ethyl alcohol; a headspace in the chamber located above the solution in the chamber; a headspace heating member having a resistance heater on the conductive body and a heating surface facing the headspace; the headspace heating member maintaining the heating surface at a temperature higher than the temperature of the solution; an inlet tube having an air inlet end located outside the chamber, the inlet tube extending from the inlet end into the chamber to an air outlet end in the solution; an effluent outlet tube having an effluent inlet end located in the headspace, the effluent outlet tube extending from the inlet end out of the chamber to an effluent outlet end located outside the chamber; wherein the headspace heating member heats alcohol-water effluent in the headspace.

8. The breath test simulator of claim 7 including an immersion heater located in the liquid solution.

9. The breath test simulator of claim 7 wherein the outlet tube is proximate the headspace heating member, wherein the heating member heats the outlet tube to heat effluent in the tube.

10. The breath test simulator of claim 7 including a temperature sensor on the conductive body and a set point switch responsive to the sensor to activate and deactivate the resistance heater.

11. The breath test simulator of claim 10 wherein the conductive body is aluminum and includes a black heating surface facing the headspace.

12. A breath test simulator for producing breath test effluent having a controlled concentration of ethyl alcohol, the simulator comprising:

a container defining a closed chamber;

a solution comprising ethyl alcohol in the chamber;

a headspace in the chamber located above the solution;

effluent in the headspace;

a blow tube having an inlet end located outside the chamber and an outlet end located in the solution in the chamber;

an effluent outlet tube having an inlet end located in the headspace and an outlet end located outside the chamber;

a solution heater for heating the solution in the chamber;

a headspace heater for heating the effluent in the headspace, wherein the solution heater maintains the solution in the chamber at a desired temperature and the effluent heater maintains the effluent in the headspace at a desired temperature; and the headspace heater including a heating member facing the headspace and the headspace heater maintaining the heating member at a temperature greater than the temperature of the solution.

13. The breath test simulator of claim 12 wherein the outlet tube is proximate the headspace heater.

14. A method of producing a breath test effluent having a known ethyl alcohol concentration for calibrating a breath test analyzer, the method comprising the steps of:

A) flowing air though a solution having a known ethyl alcohol concentration to form a breath test effluent sample having a known ethyl alcohol concentration;

B) collecting the breath test effluent sample in an effluent chamber;

C) heating the breath test effluent sample in the effluent chamber to a temperature;

D) flowing the heated breath test effluent sample from the effluent chamber to a breath test analyzer, and E) maintaining the temperature of the solution substantially equal to said temperature of the effluent sample.

15. The method of claim 14 including the step of:

F) heating a member facing the effluent chamber and radiating heat from the member into the effluent chamber to heat the effluent sample in the chamber.

16. The method of claim 14 including the steps of:
L) providing a heating member above the effluent chamber;
M) heating the heating member; and
N) radiating heat from the heating member down into the effluent chamber.

17. The method of claim 14 including the steps of:
G) providing a heating member and a heater;
H) flowing heat from the heater to the heating member by conduction to heat the heating member; and
I) radiating heat from the heating member into the effluent chamber to heat the breath test effluent sample in the chamber.

18. The method of claim 17 including the steps of:
J) positioning the heating member over the effluent chamber; and
K) radiating heat from the heating member down into the effluent chamber.

* * * * *

UNITED STATES PATENT AND TRADEMARK OFFICE
CERTIFICATE OF CORRECTION

| | | |
|---|---|---|
| PATENT NO. | : 7,404,311 B2 | Page 1 of 1 |
| APPLICATION NO. | : 11/530489 | |
| DATED | : July 29, 2008 | |
| INVENTOR(S) | : Guth et al. | |

It is certified that error appears in the above-identified patent and that said Letters Patent is hereby corrected as shown below:

Title page Item [75]

Column 1, replace "Richard U Guth" with --Richard U. Guth--.

In the Specification:

Column 4, Line 26, insert --as-- between "C." and "described".

Signed and Sealed this

Sixteenth Day of September, 2008

JON W. DUDAS
*Director of the United States Patent and Trademark Office*